(12) United States Patent
Herring

(10) Patent No.: US 7,364,289 B1
(45) Date of Patent: Apr. 29, 2008

(54) SHADES WITH BLADES

(76) Inventor: James Oldham Herring, 202 S. Blvd., Anderson, SC (US) 29621

( * ) Notice: Subject to any disclaimer, the term of this patent is extended or adjusted under 35 U.S.C. 154(b) by 0 days.

(21) Appl. No.: 11/544,397

(22) Filed: Dec. 22, 2006

(51) Int. Cl.
*B60S 1/56* (2006.01)
*B60S 1/22* (2006.01)

(52) U.S. Cl. .............. 351/158; 15/250.001; 15/250.27; 15/250.3; 351/41

(58) Field of Classification Search .......... 15/250.001, 15/250.3, 250.27, 250.18; 351/41, 158
See application file for complete search history.

(56) References Cited

U.S. PATENT DOCUMENTS

| | | | | |
|---|---|---|---|---|
| 2,329,757 A | * | 9/1943 | Greenfield | 15/250.28 |
| 2,888,703 A | * | 6/1959 | Karwowska | 15/250.27 |
| 3,754,298 A | * | 8/1973 | Menil | 15/250.3 |
| 4,789,233 A | * | 12/1988 | Arsenault et al. | 351/158 |
| 6,640,379 B1 | * | 11/2003 | Scribner | 15/250.3 |
| 6,722,766 B1 | * | 4/2004 | Myette | 351/158 |

* cited by examiner

*Primary Examiner*—Gary K Graham

(57) ABSTRACT

What is unique and special about my Shades with Blades is not only is it a safety necessity but also all working parts that make the wipers actually work are going to be hidden inside frames, making them look just like another bad ass pair of biker riding glasses until bad weather sets in. Now, no worry as long as you have a pair of Shades with Blades by James Herring, an old school biker who rides is Panhead year round. Be safe.

1 Claim, 3 Drawing Sheets

*Wipers Shown in Mid-Stroke*

*Wiper Drive Mechanism and Cover*

1. *Hollow Frame*
2. *Micro Motor With Dual Right Angle Shafts*
3. *Micro Battery Compartment in Arm*
4. *On/Off Switch*
5. *Wiper Shaft*
6. *Micro Wiper Blades*
7. *Power Linkage to Wipers*
8. *Cam*
9. *Bellcrank*
10. *Frame Cover*

Front View with Wipers "Parked"

Wipers Shown in Mid-Stroke

Side View with Wipers "Parked"

Wiper Drive Mechanism and Cover

1. Hollow Frame
2. Micro Motor With Dual Right Angle Shafts
3. Micro Battery Compartment in Arm
4. On/Off Switch
5. Wiper Shaft
6. Micro Wiper Blades
7. Power Linkage to Wipers
8. Cam
9. Bellcrank
10. Frame Cover

SHADES WITH BLADES

Biker glasses for the day you get caught in the rain. These glasses will have wiper blades that clear the rain from the lenses. There will be both clear and tinted lenses for anytime riding. With the growing popularity of riding, this is becoming a necessity. Charity rides and biker rallies are not always lucky with the weather.

The motor will be placed in the bridge of the glasses. The wires will run down the arms with a small toggle switch on the side. The battery is similar to a watch battery, maybe smaller. These glasses will become a fashion statement as well as a clear necessity for all bikers.

BACKGROUND OF INVENTION

My invention pertains to safety while riding your scooter in extreme weather conditions as well as a perfect day. You have to have eye protection while you are on your scooter. Now we have not only eye protection but eye protection with safety in mind as these Shades with Blades come to life. That I know of there is a few similar inventions: Eyeglass Wiper Attachable Eyeglass Wipes, Shades of Fun Windshield Wiper Sunglasses from 1970s.

BRIEF SUMMARY DESCRIPTION

Shades with Blades is a unique pair of biker riding glasses that come equipped with micro wiper blades. What is unique about my Shades with Blades is that they look just like a bad pair of shades until it starts to rain on you; then these shades become shades with blades. All you have to do is mash a small button on the left arm of your Shades with Blades and two micro wiper blades will drop down from the top of your frames to begin clearing the rain from your lenses so that you will be able to continue on your journey "SAFE." When rain stops, all you do is again mash a button on the arm of your Shades with Blades and the wiper blades will retract back up into the top of your frames, making them one of a kind riding glasses.

BRIEF DESCRIPTION OF FIG. 1

As you can see, this is a front view of Shades with Blades with the micro-wipers in the off position. (1) is just pointing out the rear piece of the 2-piece frames. (6) is indicating the micro wiper blades.

BRIEF DESCRIPTION OF FIG. 2

Figure 1:
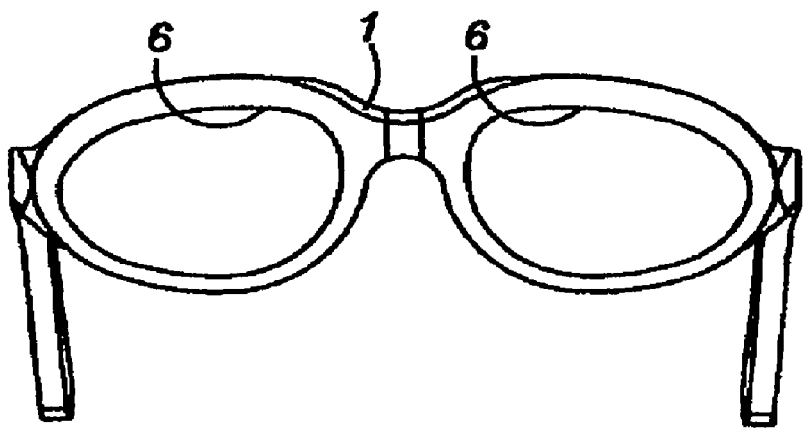
Figure 2:
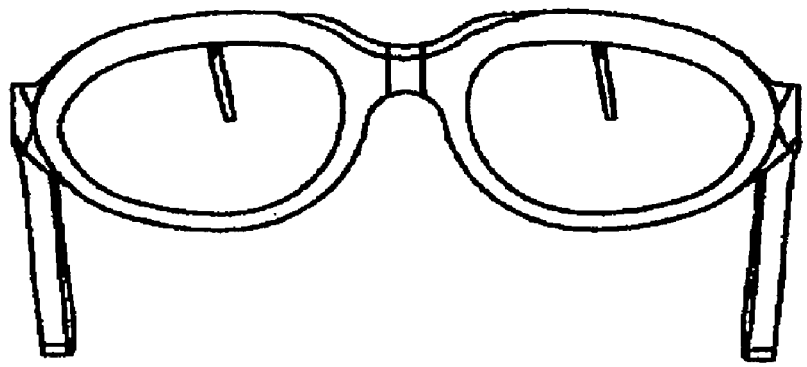

FIG. 2 is another front view of Shades with Blades with the micro wipers in the on position. The blades are actually in mid-stroke.

BRIEF DESCRIPTION OF FIG. 3

Figure 3:
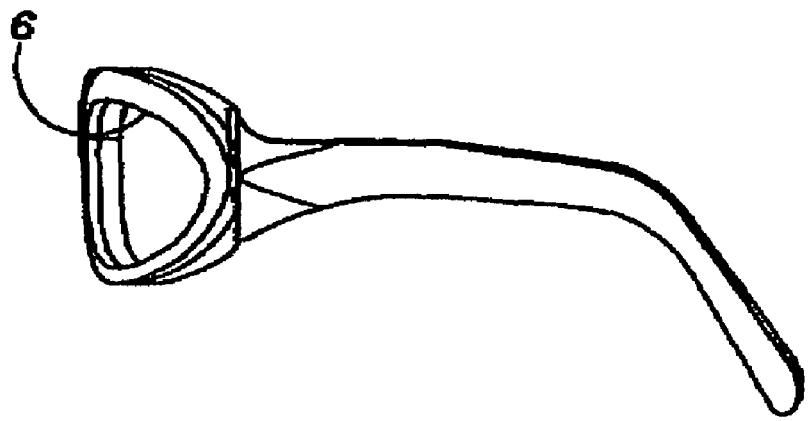

FIG. 3 is a side view of Shades with Blades showing that Shades with Blades looks like a regular pair of "bad sunglasses." The ON/OFF switch is a button located on the left arm. The micro-wiper blades in the OFF position will rest in the top side of the frames out of eyesight.

BRIEF DESCRIPTION OF FIG. 4

Figure 4:
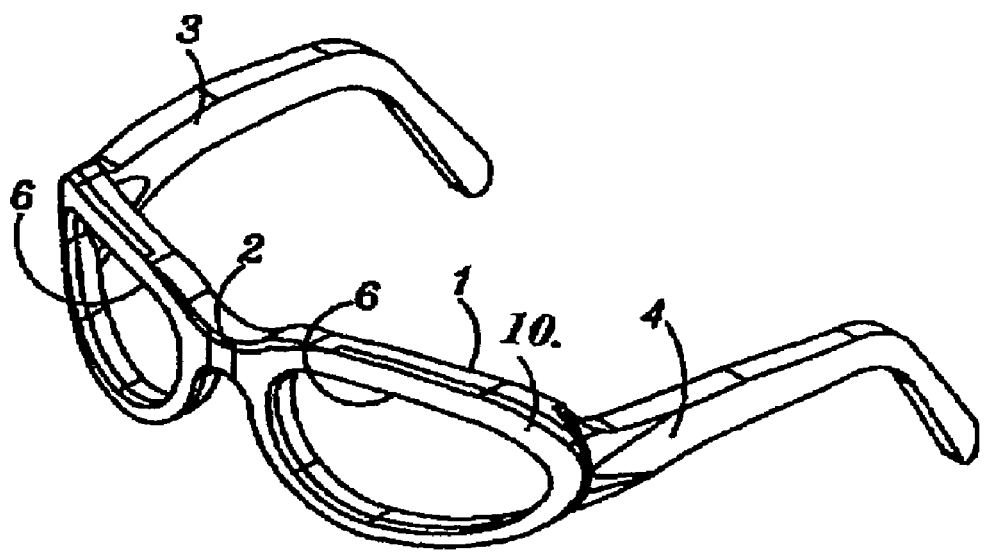

FIG. 4 is the way the Shades with Blades will look. The parts are numbered as follows: (1) Rear Piece of the 2-piece frame; (2) Micro-motor that will make everything run; (3) Micro-battery or power source inside the arm of the Shades with Blades; (4) ON/OFF micro-switch also in the arm of the Shades with Blades; (6) Pair of micro-wiper blades; (10) the front piece of the 2-piece frame.

BRIEF DESCRIPTION OF FIG. 5

Figure 5:
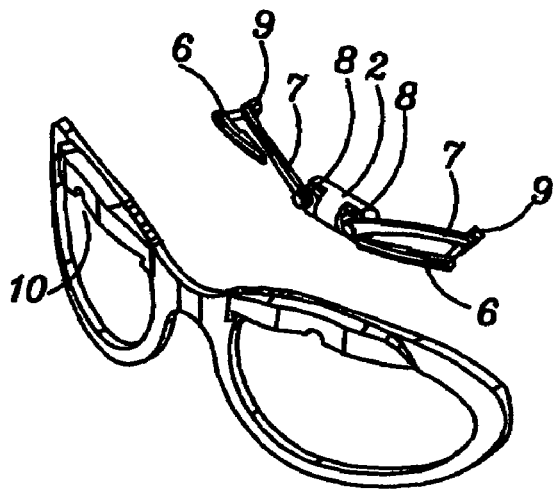

FIG. 5 breaks down the components of the Shades with Blades. The working parts attach to the Front Piece frame (10); the micro-motor is labeled (2); the wiper blades (6); linkage over from micro-motor and disc to the wiper shaft (7); cam or disc that will operate the wipers (8); micro-wiper shaft (9) that the micro-wipers will pop onto. The wiper blades (6) are designed for quick release from the shaft (9) so the wiper blades can easily be replaced when they wear out.

DETAILED DESCRIPTION OF INVENTION

Shades with Blades is a "Bad As Pair of Biker Riding Glasses." My Shades with Blades are riding glasses equipped with electric micro wiper blades. These wiper blades will drop down from the top of the frames to clear your lenses when rain starts coming down on you while you are riding, working, etc., to keep your vision clear so that you may be safe. When the rain stops, blades will retract back up into the top of your frames. What is special about my Shades with Blades is that all working parts (such as micro motor, micro battery, power cord to shafts, power to on/off switch) are hidden inside the frames. All we do is miake our frames two pieces and put working parts inside two piece frames. Now instead of several pairs of glasses, only one pair of glasses is needed for rain, sleet, shine, snow, and yes, day or night use. All lenses will be sky blue, yellow, or red so they will cut out brightness during the day but enable you to see out of them at night.

What is claimed is:

1. In combination, a pair of sunglasses and a wiper assembly;

the sunglasses comprise an elongated, two piece, hollow frame defined by a hollow rear piece with attached front cover and first and second arms extending from opposite ends of the frame; and the wiper assembly is mounted within the hollow frame, said wiper assembly comprises a micro motor positioned intermediate said ends, a cam driven by said motor, a first linkage arm extending from said cam towards the first arm to a first crank, a second linkage arm extending from said cam towards the second arm to a second crank, a first wiper shaft driven by said first crank, a second wiper shaft driven by said second crank, a first wiper blade releasably mounted to said first wiper shaft, a second wiper blade releasably mounted to said second wiper shaft, a battery provided within a compartment in the first arm as a power source for the motor and a switch with on/off positions is provided in the second arm to control motor operation;

wherein in the on position of the switch, the motor is activated to drop the wiper blades down from within a top of the hollow frame to wipe the lenses of the sunglasses and in the off position of the switch, the blades are retracted back up within the top of the hollow frame such that they are hidden.

\* \* \* \* \*